United States Patent
Tan (10) Patent No.: US 7,356,368 B2
(45) Date of Patent: Apr. 8, 2008

(54) LIGHT-ACTIVATED ANTI-INFECTIVE COATINGS AND DEVICES MADE THEREOF

(75) Inventor: Sharon Mi Lyn Tan, Allston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/896,193

(22) Filed: Jul. 21, 2004

(65) Prior Publication Data

US 2006/0100568 A1    May 11, 2006

(51) Int. Cl.
*A61N 1/30* (2006.01)
*A61L 33/00* (2006.01)

(52) U.S. Cl. .................................... 604/20; 427/2.24

(58) Field of Classification Search ............... 604/20, 604/93.01; 424/422, 423; 523/122; 427/2.24
See application file for complete search history.

(56) References Cited

U.S. PATENT DOCUMENTS

| | | | |
|---|---|---|---|
| 4,657,543 A | 4/1987 | Langer et al. | |
| 4,925,668 A | 5/1990 | Khan et al. | |
| 5,013,306 A | 5/1991 | Solomon et al. | |
| 5,019,096 A | 5/1991 | Fox, Jr. et al. | |
| 5,263,992 A | 11/1993 | Guire | |
| 5,399,168 A | 3/1995 | Wadsworth, Jr. et al. | |
| 5,445,608 A * | 8/1995 | Chen et al. | 604/20 |
| 5,451,424 A | 9/1995 | Solomon et al. | |
| 5,470,307 A * | 11/1995 | Lindall | 604/20 |
| 5,707,366 A | 1/1998 | Solomon et al. | |
| 5,728,751 A | 3/1998 | Patnaik | |
| 6,058,937 A | 5/2000 | Doiron et al. | |
| 6,107,326 A | 8/2000 | Jori | |
| 6,107,416 A | 8/2000 | Patnaik et al. | |
| 6,165,440 A | 12/2000 | Esenaliev | |
| 6,176,842 B1 | 1/2001 | Tachibana et al. | |
| 6,179,817 B1 | 1/2001 | Zhong | |
| 6,190,315 B1 | 2/2001 | Kost et al. | |
| 6,234,990 B1 | 5/2001 | Rowe et al. | |
| 6,261,271 B1 | 7/2001 | Solomon et al. | |

(Continued)

FOREIGN PATENT DOCUMENTS

WO    WO 96/23543    8/1996

(Continued)

OTHER PUBLICATIONS

Tachibana et al, Application of Ultrasound Energy as a New Drug Delivery System; Jpn. J. Appl. Phys. vol. 38 (1999) pp. 3014-3019.

(Continued)

*Primary Examiner*—Sharon E. Kennedy
(74) *Attorney, Agent, or Firm*—Hoffman & Baron, LLP (57) ABSTRACT

An implantable medical device is provided including a vascular access device and a coating on at least one of an inner surface and an outer surface of the vascular access device. The coating includes: (a) a polymeric component including at least one of a light reactive moiety and a sound reactive moiety; and (b) at least one therapeutic agent releasably associated with the polymeric component, wherein a rate of release of the therapeutic agent is controlled by in situ exposure of the medical device to at least one of a light energy source and an ultrasound energy source.

21 Claims, 5 Drawing Sheets

U.S. PATENT DOCUMENTS

| | | | |
|---|---|---|---|
| 6,338,904 | B1 | 1/2002 | Patnaik et al. |
| 6,368,611 | B1 | 4/2002 | Whitbourne et al. |
| 6,444,194 | B1 | 9/2002 | Robinson et al. |
| 6,491,657 | B2 | 12/2002 | Rowe et al. |
| 6,527,759 | B1 | 3/2003 | Tachibana et al. |
| 6,540,717 | B2 | 4/2003 | Sherry |
| 6,562,295 | B1 * | 5/2003 | Neuberger .................. 422/22 |
| 6,620,154 | B1 | 9/2003 | Amirkhanian et al. |
| 6,624,245 | B2 | 9/2003 | Wallace et al. |
| 6,713,568 | B1 | 3/2004 | Patnaik et al. |
| 2002/0019369 | A1 | 2/2002 | Li et al. |
| 2003/0092667 | A1 | 5/2003 | Tachibana et al. |
| 2003/0204141 | A1 | 10/2003 | Nock et al. |
| 2007/0154518 | A1 * | 7/2007 | Falotico et al. ............. 424/424 |

FOREIGN PATENT DOCUMENTS

| | | |
|---|---|---|
| WO | WO 98/06340 | 2/1998 |
| WO | WO 98/52610 | 11/1998 |
| WO | WO 00/78854 | 12/2000 |
| WO | WO 01/00248 | 1/2001 |
| WO | WO 01/28606 | 4/2001 |
| WO | WO 01/87416 | 11/2001 |

OTHER PUBLICATIONS

Polymeric Drug Delivery-A Brief Review; http://www.drugdel.com/polymer.htm; pp. 1-8, printed Sep. 15, 2004.

Rhine et al.; Polymers for Sustained Macromolecule Release: Procedures to Fabricate Reproducible Delivery Systems and Control Release Kinetics; Journal of Pharmaceutical Sciences; vol. 69, No. 3; Mar. 1980; pp. 265-270.

Liu et al; Synthesis and Characterization of Biocompatible Poly(Lactide-*b*-OEGMA); Polymer Preprints; vol. 43, No. 2; Fall 2002; pp. 245-246.

Kim et al.; Poly(ethylene oxide)-poly(propylene oxide)-poly(ethylene oxide)/poly(ε-caprolactone) (PCL) amphilphilic block copolymeric nanospheres II. Thermo-responsive drug release behaviors; Journal of Controlled Release; vol. 65; 2000; pp. 345-358.

Huh et al.; Synthesis and characterization of poly(ethylene glycol)/poly(L-lactic acid) alternating multiblock copolymers; Polymer; vol. 40; 1999; pp. 6147-6155.

Kim et al.; Dynamic Swelling Behavior of pH-Senstive Anlonic Hydrogels Used for Protein Delivery; Journal of Applied Polymer Science; vol. 89; 2003; pp. 1606-1613.

Lowell et al.; Venous Access Preoperative, Operative, and Postoperative Dilemmas; http://www.meditheses.com/articles/01-02-a1.htm; printed Sep. 16, 2003; pp. 1-13.

Brown, Sharon, M.S., R.Ph.; Complications with the Use of Venous Access Devices; http://uspharmacist.com/oldformat.asp?url=newlook/files/feat/acf2ff9.htm; printed Sep. 15, 2003; pp. 1-5.

Common Types of CVADs; A PICC or PICC Line; Choosing and Living with CVAD.

Tian, et al.; Design and Synthesis of Amphiphilic Poly(ethylene glycol) Derivatives as Micellar Drug Delivery Systems; Polymer Preprints; vol. 43, No. 2; 2002; pp. 719-720.

Langer et al.; Chemical and Physical Structure of Polymers as Carriers for Controlled Release of Bioactive Agents: A Review; Rev. Miacromol. Chem. Phys., vol. C23, No. 1; 1983; pp. 61-126.

Kost, Joseph; Ultrasound induced delivery of peptides; Journal of Controlled Release; vol. 24; 1993; pp. 247-255.

Kost et al.; Ultrasound-enhanced polymer degradation and release of incorporated substances; Proc. Natl. Acad. Science; USA; vol. 86; Oct. 1989; pp. 7663-7666.

Aschkenasy et al.; A Hydrophobic Water Absorbing Matrix for Ultrasonically Controlled On-Demand Drug Delivery; Proceed. Int'l. Symp. Control. Rel. Bioact. Mater.; vol. 28; 2001; pp. 311-312.

Krinick et al.; A polymeric drug delivery system for the simultaneous delivery of drugs activatable by enzymes and/or light; J. Biomater. Sci. Polymer Edn.; vol. 5, No. 4; 1994; pp. 303-324.

Jiang et al.; Template-Directed Preparation of Macroporous Polymers with Oriented and Crystalline Arrays of Voids; J. Am. Chem. Soc.; vol. 121; 1999; pp. 11630-11637.

Veenstra et al.; Efficacy of Antiseptic-Impregnated Central Venous Catheters in Preventing Catheter-Related Bloodstream Infection; JAMA; vol. 281, No. 3; Jan. 20, 1999; pp. 261-267.

Okino, et al.; In Situ Hydrogelation of Photoreactive Gelatin and Drug Release; Abstract No. 29 in International Journal of Artificial Organs; vol. 23, No. 8; 2000; pp. 534.

Pedley et al; Hydrogels in Biomedical Applications; The British Polymer Journal; Sep. 1980; vol. 12, pp. 99-110.

Kwon et al.; Enhanced tumor accumulation and prolong circulation times of micelle-forming poly(ethylene oxide-aspartate) block copolymer-adriamycin conjugates; Journal of Controlled Release; 1994; vol. 29, pp. 17-23.

\* cited by examiner

LIGHT-ACTIVATED ANTI-INFECTIVE COATINGS AND DEVICES MADE THEREOF

FIELD OF THE INVENTION

The present invention relates generally to implantable medical devices having a biocompatible polymer coating for delivery of therapeutic agents. More particularly, the present invention relates to an implantable medical device having a biocompatible polymer coating including at least one therapeutic agent whereby the therapeutic agent is released from the coating by exposure to at least one of ultrasound energy and light energy.

BACKGROUND OF THE INVENTION

Central vascular access devices (CVADs) are medical devices that are implanted into a patient's vascular system and are typically used in applications which provide a means for repeated access to a patient's vascular system. Applications for CVADs are varied and include, for example, intravenous feeding, intravenous drug delivery, and extracorporeal protocols. Specific applications include chemotherapy treatments, intensive antibiotic treatment, prolonged IV feeding, and extracorporeal blood treatment protocols, such as hemodialysis, hemofiltration, and apheresis.

CVADs having an exterior component (located outside the skin of a patient) are convenient to use and may be used safely by skilled practitioners who use sterile cannulas to access the CVAD and who provide sufficient maintenance in the form of regular flushing and dressing changes. However, an added risk of infection exists due to the presence of the exterior component. Specifically, the external component may serve as a route of exposure to airborne contaminants such as bacteria.

Figure 1:
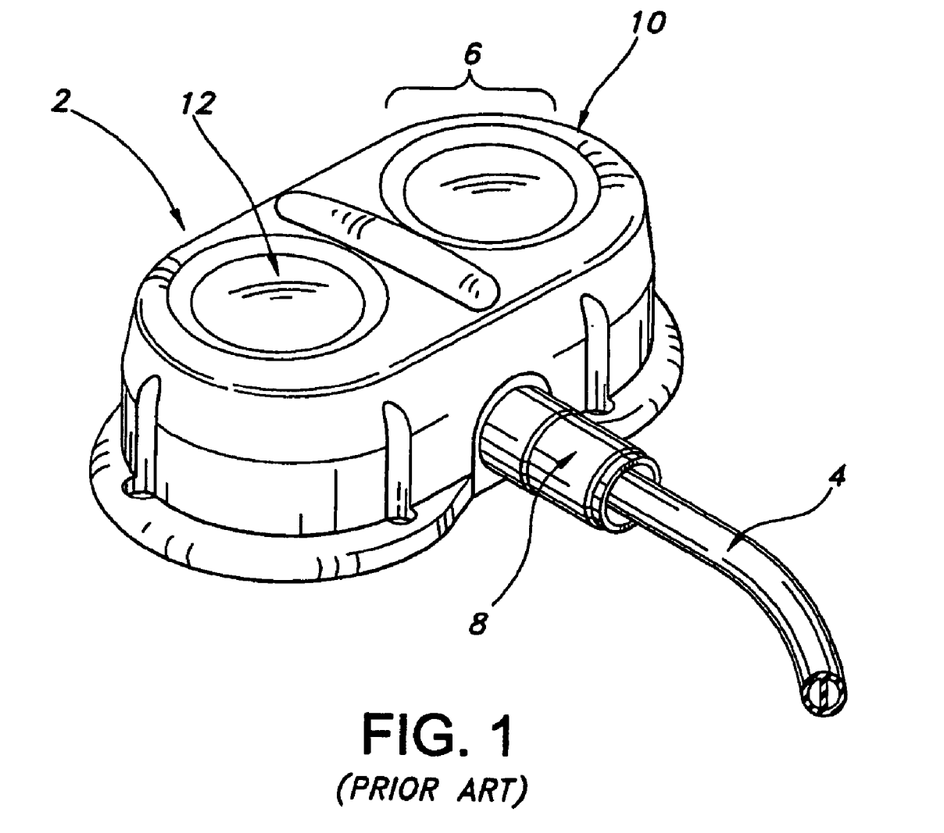
FIG. 1 is a perspective view of a conventional implantable A-V port.

Total implantation venous access devices, also referred to herein as TIVADs are a variety of vascular access devices that are implanted into a patient's vascular system but that do not have any exterior components. The entire device is implanted under the patient's skin. TIVADs have become used more routinely, where possible, as opposed to other central vascular access devices (CVADs) having an exterior component. An example of a TIVAD is an arterial-venous (A-V) port used in accessing the circulatory system, for example, in performing dialysis treatments. The port is accessed through the skin by percutaneous placement of a HUBER needle or other connecting tube. An example of a conventional port is shown in FIG. 1. The A-V port, referred to generally as reference numeral 2, includes a lumen catheter 4 coupled to one or more reservoir access port 6 via a catheter connector 8. The catheter 4 resides in the vein. The port 6 includes an impenetrable housing 10 defining a reservoir for fluids. The housing 10 includes an opening for receiving a plastic or metal disk having a septum 12 in the center. The septum 12 is a needle penetrable elastometric material and acts as a portal to the reservoir. Further examples of commercial ports include those disclosed in U.S. Pat. No. 5,399,168, or VAXGEL implantable ports (available from Boston Scientific, Natick, Mass.).

TIVADs such as ports require less maintenance that other CVADs. For example, a properly functioning port may require flushing only once a month. Furthermore, no external dressing is necessary for such ports. An advantage of using TIVADs over other CVADs is the reduced risk of infection arising from the protective skin barrier which prevents any possible exposure to airborne contamination. A further advantage of TIVADs over CVADs generally is greater patient acceptance.

Risks associated with the use of CVADs include local complications such as thrombosis and thrombophlebitis, as well as systemic complications including embolisms, pulmonary edema and bloodstream infections. Although the risk of infection is reduced in TIVADs as compared to other CVADs, it is still possible for a patient to experience an infection at the port, particularly the area where the port is accessed.

The average time a TIVAD-type A-V port remains useful for A-V access is about two years. During these two years, infection will develop in around 20% of patients, and often leads to removal of the port. In this case, A-V access has to be reestablished. Often, this means finding another site for A-V access and waiting a period of time of up to three weeks before a normal hemodialysis schedule can be resumed.

Infection of the A-V port has been recorded as a major cause of death in patients receiving dialysis treatments. There are principally three ways in which an infection can be introduced during A-V access set up or the hemodialysis procedure itself. First, bacteria can be implanted with the A-V access device itself during a break in aseptic technique. Second, bacteria may already be present on the surface of the device. Third, bacteria can be transmitted from external sources, such as central venous catheters and needles. The entry site for infection is typically the puncture site.

The course of treatment for infections related to CVADs depends upon the type of medical device, the condition of the patient, and the identity of the bacteria causing the infection. The most common infectious agents are: *staphylococcus aureus, pseudomonas aeruginosa*, and *staphylococcus epidermis*. These agents have been identified in over 75% of all reported vascular infections. Both *staphylococcus aureus* and *pseudomonas aeruginosa*, show high virulence and can lead to clinical signs of infection early in the post-operative period (less than four months). It is this virulence that leads to septicemia and is one main factor in the high mortality rates. *Staphylococcus epidermis* is described as a low virulence type of bacterium. It is late occurring, which means it can present clinical signs of infection up to five years post-operative. This type of bacterium has been shown to be responsible for up to 60% of all vascular graft infections.

Vascular port infections are difficult to treat with the standard course of oral antibiotics. Accordingly, infections of this type often require total graft excision, debridement of surrounding tissue, and revascularization through an uninfected route. It would be advantageous for implantable medical devices, such as ports, to be provided with a mechanism to deliver a therapeutic agent to address such infections, at the site of infection.

Figure 2:
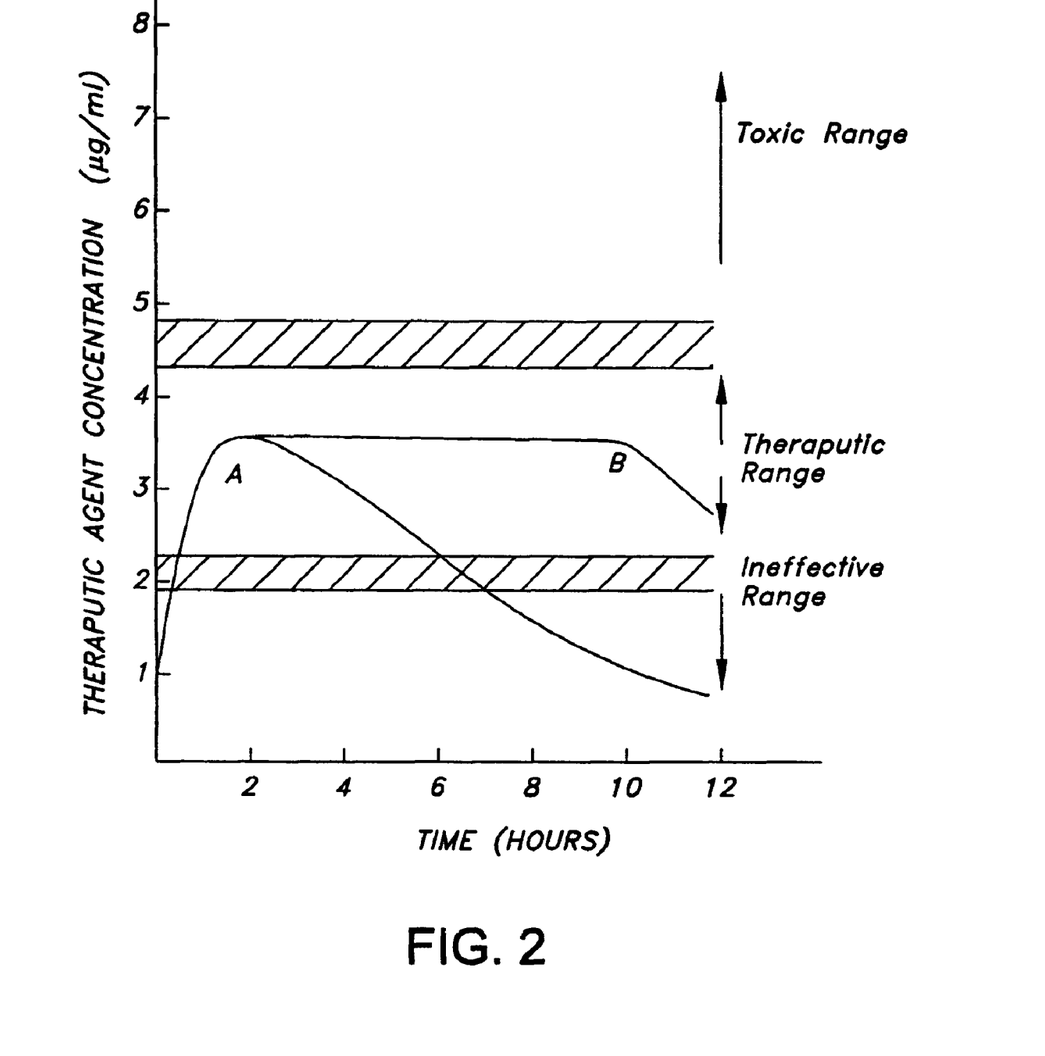
FIG. 2 is a graph showing a typical release profile for a conventional dosing scheme as compared to that of a sustained release dosing scheme.

Generally, it is known that certain design parameters are critical to proper delivery of therapeutic agents. Typically, they are: (1) delivering the agent to the target tissue; (2) supplying the agent in the correct temporal pattern for a predetermined period of time; and (3) fabricating a delivery system that provides the desired spatial and temporal pattern. Controlled or sustained release delivery systems are intended to manipulate these parameters to achieve the aforementioned advantages when compared to conventional dosing. A typical drug concentration versus time profile for a conventional parenteral or oral dosage form (A) and an idealized sustained drug delivery system (B) might look as shown in FIG. 2.

A disadvantage of presently available methods for providing therapeutic agents on medical device substrates is the lack of a means to control the rate of release of the therapeutic agent. For example, in conventional biodegradable polymers, a steady state rate or sustained release of drug occurs, based on, inter alia, the rate of degradation of the polymer. Accordingly, there is no control over the time or rate of delivery of the therapeutic agent. It is possible, using these systems, for the therapeutic agent to be depleted by the time it is needed by the patent. Thus, the patient is dosed with therapeutic agent even if there is no infection. Furthermore, an active infection may require a larger dose than is delivered by sustained release of the therapeutic (i.e. antimicrobial) agent.

It would therefore be advantageous, for an implanted medical device such as a CVAD, in particular a TIVAD, to provide variable drug release, so as to increase the dose of the therapeutic agent when necessary to address an active infection.

SUMMARY OF THE INVENTION

The present invention provides a coating for a medical device including a polymeric structure including at least one therapeutic agent, wherein a rate of release of the therapeutic agent from the polymeric structure is regulated by in situ exposure of the coating to at least one of ultrasound energy and light energy. When used as a coating on a medical device implanted in a patient, the coating provides the therapeutic agent to the patient on an as-need basis.

In accordance with the present invention, an implantable medical device is provided including a vascular access device and a coating on at least one of an inner surface and an outer surface of the vascular access device. The coating includes: (a) a polymeric component including at least one of a light reactive moiety and a sound reactive moiety; and (b) at least one therapeutic agent releasably associated with the polymeric component, wherein a rate of release of the therapeutic agent is controlled by in situ exposure of the medical device to at least one of a light energy source and an ultrasound energy source.

Also provided is a method of treating a patient including the steps of: (a) implanting a medical device of the invention intradermally into a patient in need thereof; and (b) releasing the therapeutic agent to the patient by intra- or extra-dermal exposure to at least one of a light energy source and an ultrasound energy source.

DETAILED DESCRIPTION OF THE INVENTION

The present invention is directed to a medical device including a coating having a polymeric component and a releasable therapeutic agent associated therewith. The coating uses one or more polymers to mechanically hold and/or chemically bond one or more therapeutic agents to the polymer. The coatings are placed on at least part of inner and/or outer surfaces of a medical device, preferably a TIVAD, before implantation into a patient in need thereof. The rate of release of the therapeutic agents is controlled by exposure to at least one of a light or an ultrasound energy source.

Suitable Polymers

Those polymers useful in preparing coatings of the present invention include a wide variety of known polymers. Although the mechanism of action of the individual polymer-therapeutic agent combinations may differ, common among the polymers used in the present invention are the properties of chemical and physical stability, biological inertness, and processability. Further desirable properties for use in coating the septum part of an A-V port, include a low glass transition temperature which provides the characteristic, inter alia, of pliability.

Useful polymeric materials include polymers, copolymers, block polymers and mixtures thereof. Among the known useful polymers or polymer classes which meet the above criteria are: poly(glycolic acid) (PGA), poly(L-lactic acid) (PLLA) (PLA), polyoxalates, poly($\alpha$-esters), polyanhydrides, polyacetates, polycaprolactones, poly(orthoesters), polyamino acids, polyurethanes, polycarbonates, polyiminocarbonates, polyamides, poly (alky cyanoacrylates), and mixtures and copolymers thereof. Additional useful polymers include, stereopolymers of L- and D-lactic acid, copolymers of 1,3 bis(p-carboxyphenoxy) propane and sebacic acid, sebacic acid copolymers, copolymers of caprolactone, poly(lactic acid)/poly(glycolic acid)/polethyleneglycol terpolymers, copolymers of polyurethane and poly (lactic acid), copolymers of $\alpha$-amino acids, copolymers of $\alpha$-amino acids and caproic acid, copolymers of $\alpha$-benzyl glutamate and polyethylene glycol, copolymers of poly succinic acid and poly(glycols), polyphosphazene, polyhdroxy-alkanoates and mixtures thereof. Binary and ternary systems are contemplated.

Preferred are poly(ethylene oxide) (PEO), poly(ethylene glycol) (PEG), poly(propylene glycol) (PPG), poly (L-lactic acid) (PLLA), poly($\epsilon$-caprolactone), poly($\alpha$-amino acids), polyurethanes, poly(vinyl alcohol) (PVA) poly(vinyl pyrrolidone), poly hydroethyl methacrylate, and copolymers and block polymers thereof.

Some exemplary polymers which can be used in forming coatings for use in the present invention may be generally categorized as follows:

I. Polyesters a) poly ($\epsilon$-caprolactone) (PCL):

b) poly (glycolic acid) (PGA):

c) poly (L-lactic acid) (PLLA):

d) poly (lactic acid-co-glycolic acid) (PGA):

e) poly (lactic acid-co-ε-caprolactone) (PLACL):

II. Poly (ethylene glycol), PEG Block Copolymers (Also Referred to as poly(ethylene oxide) (PEO)
 a) PLA-PEG diblock copolymer:

b) PLA-PEG-PLA triblock copolymer:

c) Poly (orthoesters):

Within aqueous environments, the ortho ester groups are hydrolyzed to form pentaethyritol and proprionic acid. This is controlled by introducing basic or acid components into the matrices.

III. Polyanhydrides
 a) poly[1,3 bis(p-carboxyphenoxy propane)], where x=3
 poly[1, bis(p-carboxyphenoxy hexane)], where x=6 b) poly (sebactic anhydride):

IV. Poly(acrylic acid) (PAA) and Derivatives, and vinyl Polymers Thereof, for Example:
 a) R=H— or CH$_3$— (methacrylic)
 R'=H— or HOCH$_2$CH$_2$— b) R=H— or CH$_3$

—R'=—CH$_2$ CH(OH)CH$_3$, —CH(CH$_3$)$_2$ c) Polyvinyl alcohol (PVA):

d) Poly(ethylene-co-vinylacetate) (PEVAc):

See, for example, Proceeding of the 28$^{th}$ International Symposium on Controlled Release of Bioactive Materials, San Diego, Calif., C. Aschkenasy and J. Kost, p. 311-312 (June 2001).

V. Poly(amino acids) and Copolymers
  (a) poly (lysine):

b) Poly (lactic acid-co-lysine):

VI. Polyurethanes and Block Copolymers
  a) R=(CH$_2$)$_n$
  n 4-6

Commercially available polyurethanes include BIOMER, ACUTHANE (available from Dow Chemical Co., PELLETHANE (available from Dow Chemical Co., Wilmington, Del.), and RIMPLAST.

VII. Poly(dimethylsiloxanes)

Further examples of suitable commercially available polymers include: PLURONIC (available from BASF Corp., Ludwigshafen, Germany); MEDISORB, ELVAX40P (ethylene vinyl acetate) and BIODEL (available from Dupont Corp., Wilmington, Del.); and Polymer No. 6529C (Poly(lactic acid)) and Polymer No. 6525 (poly(glycolic acid)) available from Polysciences Inc., Warrington, Pa.

In one aspect of the invention, polymers used are polyvinyl alcohol (PVA), polyvinyl pyrrolidone, polyethylene oxide, polyhydroxyethyl methacrylate alone or in combination.

In a preferred aspect of the invention, the polymers are FDA approved for use in the body. Mixtures of polymers as well as layers of polymers are contemplated in the coatings used in the present invention. As will be discussed further herein, known polymers may be used or be derivatized so as to provide a coating in which the rate of release of a therapeutic agent contained therein can be controlled, directly at a point of infection.

Polymer Systems Useful in the Invention

Known polymer systems which mechanically hold therapeutic agent therein, deliver the agent in a controlled release fashion based on the structural and morphological configuration of the polymer. Specifically, transport of particles (such as therapeutic agents) through pores in polymeric membranes occurs by mass transit mechanisms such as diffusion and convection. The mass transport of particles depend on whether or not the polymeric structures contain pores, and if so, what size pores. Macroporous membranes having relatively large pores in the range of about 500 angstroms to about 1.0 microns rely primarily on convection to release particles. Examples of polymeric materials which can form macroporous membranes include polyurethanes, polyethylene glycol/poly propylene glycol copolymers and poly(lactic-co-glycolide-polyethylene).

In microporous polymer systems, in which the pore size is from about 100 angstroms to about 500 angstroms, transport phenomenon is restricted by the geometric characteristics of the porous structure and by solute in the pores partitioning the pore walls. Examples of polymeric materials which can form microporous membranes include ethylene vinyl acetate copolymer loaded with macro molecular therapeutic agent. See, for example, Rhine et al., J. of Pharmaceutical Sci., 69: 265-26 270 (1980).

Non-porous polymer systems, such as hydrogels, have internal structure based on molecular chains of entangled, cross-linked or crystalline chain networks in the polymer. As used herein a "hydrogel" is a polymeric material that swells in water without dissolving and that retains a significant amount of water in its structure. Hydrogels may deform elastically. The space between macromolecular chains is the mesh size. In these polymer systems, diffusion can be regulated to a certain extent by controlling the geometric factors such as thickness and surface area of the polymeric structure, and physiochemical parameters related to permeability of solute through the membrane. Controlling characteristics of the polymeric structure such as crystalline phase, porous structure, degree of swelling, additive concentration, mesh size of cross-linked macromolecular chains, and thermodynamic glassy/rubbery transitions, can be used to control diffusion. In particular, cross-linking and/or entangled polymer chains produces a screening effect to reduce the rate of diffusion. Hydrogels useful in the present invention include, for example, polyhydroxyethylmethacrylate, polyvinyl alcohol and the like.

Another form of polymeric system is the reservoir system in which a polymeric membrane surrounds a core of therapeutic agent. In this embodiment, a porous or non-porous polymer encapsulates therapeutic agent within micro- or nano-particles, which form micro-containers or micelles for the therapeutic agent. Non-limiting examples of preferred polymers for use in this embodiment include poly(ethylene glycol) (PEG), poly(acrylic acid) (PAA) and poly(vinyl alcohol) (PVA) or co-polymers or block polymers thereof. See, for example, Tian and Uhrich, *Polymer Preprints*, 43(2): 719-720 (2002). Preferably, the polymer is amphiphilic, containing controlled hydrophobic and hydrophilic balance (HLB) which facilitate organization of the polymer into circular micelles. The therapeutic agent is contained in the micelles for later release. Examples of suitable reservoir systems include hydrogels such as swollen poly(2-hydroxyethyl methacrylate) (PEMA), silicone networks, ethylene vinyl acetate copolymers and the like. See, for example, Pedley et al., *Br. Polymer J.*, 12: 99 (1980). Further examples include polyvinyl alcohol, polyvinyl pyrrolidone, and polyethylene oxide.

Furthermore, known polymer systems which chemically degrade so as to release therapeutic agent contained therein may be adapted for use in the invention. Specifically, polymer systems referred to as polymeric matrixes possess characteristics which promote chemical degradation or erosion of the polymer to release therapeutic agent. Chemically, there are three mechanisms for polymer erosion from a bulk matrix. First, degradation of cross-links can free polymer chains from the bulk matrix. Second, solubilization of water-insoluble polymers can occur as a result of hydrolysis, ionization, or protonation of a side group. Third, degradation of labile backbone bonds attached to the backbone structure of the polymer chain. In this mechanism, polymers having hydrolytic labile backbone or side chains contribute to the process of degradation.

Degradation of cross-links is possible if the polymer includes or is derivatized to include labile moieties in the cross-linkers such as ester or amide functional groups. Any polymeric material may be derivatized to include such labile portions using methods generally known to one having ordinary skill in the art.

Examples of polymeric matrix materials exhibiting the second type of chemical degradation include those including a pendant group that may be solubilized. Specific polymers of this type include poly(L-lysine-co-polyethyleneglycol), poly(methacrylic acid-co-methacryloxyethylglucoside) and poly(methacrylic acid-co-ethyleneglycol).

Examples of polymeric matrix materials exhibiting the third type of chemical degradation include high molecular weight water-insoluble polymers having labile bonds in the polymer backbone. These labile bonds become cleaved and the cleaved portion of the polymer is converted to small, water-soluble molecules. Alternative, a percolation technique breaks the backbone bonds causing the volume of the polymer to increase and allow therapeutic agent captured therein to flow out of the polymer. Examples of such bioerodible polymers include polylactic acid (PLA), polyglycolic acid (PGA) and lactic/glycolic acid co-polymer, polyamides, poly($\epsilon$-caprolactone), poly(orthoesters), and polyanhydrides. Further non-limiting examples of suitable polymers in forming the matrix include polyanhydrides, ethylene-vinyl acetate, poly(lactic acid), poly(glutamic acid), poly($\epsilon$-caprolactone), lactic/glycolic acid copolymers, polyorthoesters, polyamides and the like. Non-degradable polymers include ethylene-vinyl acetate and silicone.

Alternatively, it is possible to link a photosensitizer to a polymer backbone or side chain of the backbone using an appropriate linker which, when exposed to an appropriate light energy, will react to release the therapeutic agent associated therewith. In this embodiment the therapeutic agent may be linked via a side chain to the polymer backbone and the photosensitzer may be linked to the same or different polymer backbone in the vicinity of the therapeutic agent. It is also possible to attach a photosensitizer directly to the therapeutic agent, or to interpose a photosensitizer between a linker and a therapeutic agent. Examples of polymers suitable for use in this embodiment include co-polymers of N-(-2 hydroxypropyl) methacrylamide and an enzymatically degradable oligopeptide poly (L-lysine-co-polyethylene glycol).

In each of these known polymer systems, once the design criteria has been selected, it has not heretofore been known to modify the polymeric configuration in situ to alter rates of release of a therapeutic agent contained therein after implantation. Heretofore these polymer systems either did not erode at sufficiently high rates to deliver sufficient dosages or released the therapeutic agent too quickly. Additionally, although the Langer reference shows a compressed implant of a polymeric structure which is implanted independent of a medical device, it has not been known to coat a medical device with a polymeric material in which release rates of a therapeutic agent contained therein may be regulated and the therapeutic agent delivered directly to the location of the infection without first having to be circulated throughout the system. Thus, although the known polymeric systems may degrade over time, or the polymeric systems may release a therapeutic agent through diffusion through pore structures, or implanted polymeric blocks may be treated to release therapeutic agent therefrom, it has not until now been shown that a coated medical device may be exposed in situ to an energy source so as to immediately direct the release of a therapeutic agent at the site of an infection.

Ultrasound Responsive Polymeric Materials

As used herein, the term "ultrasound" or "ultrasound energy" refers to a mechanical ("acoustic" or in terms of "pressure") wave in a medium in a frequency range of from about 16 kHz to about 1 GHz. Ultrasound is a longitudinal wave form with the direction of propagation being the same as the direction of oscillation. The effects of ultrasound energy generally include compression and expansion of the propagation medium at approximately one half a wavelength distance from the wave source. This causes pressure variations in the medium. The wavelength of ultrasound is expressed by the relationship:

$$\lambda f = C$$

where:
  $\lambda$=wavelength
  f=frequency
  C=speed of propagation

It is possible to direct sufficient ultrasound energy to a particular location in the body by accounting for the mass density of the tissue being penetrated and the related half value depth. By applying ultrasound waves perpendicular to homogeneous tissue (i.e., skin), it is possible to calculate the absorption coefficient which indicates the intensity of absorption in the tissue, as follows:

$$I(X) = I_0 \cdot e^{-ax}$$

where:
  I(X)=intensity at depth X
  $I_0$=intensity at the skin surface
  a=absorption coefficient Generally, release rate is proportional to the intensity of the applied sound wave. By knowing the intensity of the wave at the surface of the skin, an absorption coefficient for a known depth of X can be realized by solving the above equation for a. A parameter relating to absorption is the half-value depth ($D_{1/2}$) which is the distance in the direction of a sound beam in which the intensity in a certain medium decreases by half. For skin, the $D_{1/2}$ is 11.1 mm at 1 MHz and 4 mm at 3 MHz.

The effects of ultrasound are related to several different physical mechanisms including thermal heating, cavitation and streaming. In thermal heating, part of the ultrasound energy applied to a polymer will be converted into heat. For example, exposure of soft tissue to an ultrasound beam of an intensity of 1 W/cm$^2$ can result in a rise in temperature of 0.5° C./s if heat conduction is discounted. Using ultrasound energy to cause controlled localized thermal heating will generate heat induced changes, including but not limited to breaking of cross-linking bonds, in the polymeric material. The application of heat under controlled conditions will thereby regulate the rate of release of the therapeutic agent by controlling the rate of diffusion of the therapeutic agent from the polymeric material, the rate of degradation of the polymeric material or a combination thereof.

In cavitation, application of ultrasound to a liquid or quasi-liquid medium gives rise to activity involving gaseous or vaporous cavities or bubbles in the medium. Cavitation may require pre-existing nuclei or bodies of gas stabilized in crevices or pores or by other means in the medium. Both stable and transient cavitation are possible. In stable cavitation, gas bubbles of a size that are resonant in the sound field generated oscillate with large amplitude. The expansion and contraction of the bubble which oscillate with the ultrasound pressure cycle causes the surrounding medium to flow in and out with a higher velocity than if the gas bubble were absent. The resonant diameter of a cavitation bubble in water at 1 MHz is about 3.5 microns. Pulsating gas bubbles resulting from such resonation are asymmetric at the air/liquid interface. The surface of such a pulsating asymmetric oscillation bubble causes a steady eddying motion to be generated in the immediate adjoining liquid, often called microstreaming. This pulsating results in localized shearing action which is strong enough to cause fragmentation of internal structures of the polymer. For example, main chain rupture may be induced by shock waves during cavitation of the liquid medium.

Acoustic streaming is the unique property of acoustic wave propagation in which time independent flow of fluid is induced by the sound filed. Without intending to be limited to any particular theory, it is believed that streaming is related to the conservation of momentum dissipated by the absorption and propagation of the wave. As a result of streaming, physical effects such as enhanced transfer of heat and mass, changes in reaction rates, and depolymerization are possible. Accordingly, using ultrasound energy to cause cavitation and/or microstreaming in a polymer system will cause the controlled alteration in structure, such as fragmentation and expansion of pore structures, so as to increase the rate of diffusion of the therapeutic agent from the polymeric material.

Additionally, chemical changes are commonly produced by cavitation. Again, without intending to be limited to any particular theory, it is believed the combination of high pressures and temperatures can generate aqueous free radicals and hydrated electrons (highly reactive chemical species) within the exposed medium by the dissociation of water vapor in the bubble during its contraction. Chemical reactions of the resultant free radicals (particularly —H and —OH radicals) with the polymeric structures are sufficient to increase the rate of degradation of the polymeric structures to release the therapeutic agent. Using ultrasound energy to cause chemical changes in a polymeric system will cause the controlled degradation of polymeric infrastructure by increasing the rate of release of the therapeutic agent from the polymeric material.

Although deep body tissue is generally opaque to light, it is usually penetrable by ultrasound waves. Accordingly, ultrasound waves emitted from a focused ultrasound transducer or a phased array can be concentrated at any location in the body. Depending on the frequency, the ultrasound transducer can cause cold cavitation, localized heating and/or streaming effects on a polymer at the focal point of exposure. Thus, it is well within the purview of the invention to initiate temperature, mechanical and/or chemical related release of therapeutic agent from a polymeric material by exposure to ultrasound.

In one embodiment of the invention, ultrasound is applied to a coating on a medical device sufficient to cause a localized and controlled temperature, mechanical and or chemical effect on at least a portion of the coating, thereby regulating the rate of diffusion of the therapeutic agent from the polymeric material, the rate of degradation of the polymeric material or a combination thereof. Accordingly, the rate of release of the therapeutic agent contained therein is regulated based on the frequency, duration and intensity of the applied wave.

In this embodiment, a polymeric material including a releasable therapeutic agent is exposed to ultrasound energy under conditions and for a time to cause at least one of the effects discussed above, sufficient to release the therapeutic agent at a desired rate.

Rate of release of therapeutic agent from the polymeric material can be regulated by varying one or more of the intensity, frequency or duration of the applied ultrasound energy. There are no particular limitations to the frequency, duration and intensity of the applied wave provided the combination is sufficient to provide the desired rate of release of the therapeutic agent while preserving the structural integrity and functionality of the medical device substrate or substrates and the therapeutic agent.

Preferably, the ultrasonic energy is generated from an ultrasound transducer. The range of intensity of ultrasound effective for producing short-term therapeutic agent release from a polymeric material is preferably from about 0.1 W/cm$^2$ to about 30 W/cm$^2$, more preferably from about 1 W/cm$^2$ to about 50 W/cm$^2$. As stated above, the rate of release of the therapeutic agent is proportional to the intensity of the applied sound wave. Thus, it is possible to increase the intensity of the applied ultrasound energy to increase the rate of release.

Preferably, the ultrasonic energy is delivered in the frequency range of from about 20 kHz to about 10 MHz and is delivered through the skin to the implanted medical device. Preferably, the frequency is in the range of from about 50 kHz to about 200 kHz. For the purposes of maximizing cavitation effects, preferably the frequency used will be about 2.5 MHz.

Duration and/or pulse cycle of the wave form will also have an effect on the amount of therapeutic released per exposure event. The duration of exposure may also be varied to regulate the rate of release. Although there is no particular limitation to the duration of exposure, for the comfort and convenience of the patient, it is desirable to minimize the time of exposure. Suitable times may range from a few seconds continuous or pulsed to an hour or more. Preferably, the exposure shall be from about 20 seconds to about 10 minutes, continuous or pulsed. It is possible to generate release rate curves for a particular polymer and therapeutic agent combination so as to be able to know the amount of time necessary to achieve the desired amount and/or rate of release of the therapeutic agent.

There are no particular limitations to the polymeric material used in these embodiments except that it should, without exposure to ultrasound or light, resist substantial erosion for at least about six months, preferably at least about one year.

In one aspect of the invention, the polymeric material used in the coating will have a sufficient number of temperature labile bonds therein so that exposure to the elevated temperatures contemplated from localized heating, results in an increase in the rate of release of therapeutic agent.

Further, in another aspect of the invention, in order to take advantage of cavitation related effects, the polymer will preferably have pores including air bubbles. In this aspect of the invention, it is desirable for the polymeric material to include a micelle surrounding, a therapeutic agent and include air bubbles therein. Preferably, the micelles are from about 0.01 to 100 microns in diameter and have a gas volume therein of from about 5% to about 30% of the volume of the micelle. Preferably, the therapeutic agent is a light activatable drug. See, for example, U.S. Pat. No. 6,527,759, which is herein incorporated by reference. Additional limitations to this embodiment include the medical device surface or substrate which is coated should be stable at the localized temperatures used to effect release of the therapeutic agent. Furthermore, the therapeutic agent used should be stable at any elevated temperatures used to either polymerize the polymeric material or to coat the medical device. Preferably, the polymeric material may be cured at or about room temperature.

In one aspect of the invention, polymers which readily release therapeutic agent through diffusion through a polymeric matrix may be derivatized using a cross-linking agent to include cross-linked internal structure which will degrade upon exposure to ultrasound energy.

In one aspect of the invention, a polymeric material used in the coating includes bonds which break upon exposure to localized elevated temperature from exposure to ultrasound energy. Examples of such bonds include ester or amide introduced into the polymer by side chain reactions such as esters or acids with amine. Examples of polymeric materials suitable for use in this embodiment include, but are not limited to, poly(L-lysine-co-polyethyleneglycol), poly (methacrylic acid-co-methacryloxyethylglucoside) and poly (methacrylic acid-co-ethyleneglycol), polylactic acid (PLA), polyglycolic acid (PGA), polyamides, poly($\epsilon$-caprolactone), poly(orthoesters), and polyanhydrides. Further non-limiting examples of suitable polymers in forming the coating include polyanhydrides, ethylene-vinyl acetate, poly (lactic acid), poly(glutamic acid), poly($\epsilon$-caprolactone), lactic/glycolic acid copolymers, polyorthoesters, polyamides and the like. Suitable cross-linking agents will be apparent to those having skill in the art.

In a further aspect of the invention, the polymeric material used in the coating includes pores which, when exposed to ultrasound energy, react by forming localized changes in the internal configuration of the pores so as to enlarge the pores and release therapeutic agent contained therein. Examples of polymeric materials suitable for use in this embodiment include, but are not limited to polyethyleneglycol/polypropylene glycol copolymers and poly(lactide-co-glycolide polyethyleneoxide).

In another aspect of this embodiment, the polymeric material is derivatized to include temperature sensitive bonds so as to increase reactivity upon exposure to the localized elevated temperatures used to release the therapeutic agent. In this embodiment, the polymeric material is derivatized to contain an ultrasound reactive component which, when exposed to ultrasound energy, will effect a controlled increase in the rate of release of the therapeutic agent from the polymeric material.

In a still further aspect of the invention, the polymeric material used in the coating includes both bonds and pores which react upon exposure to ultrasound energy so as to release therapeutic agent.

Photoreactive Polymeric Materials

In another embodiment of the invention, a coating is provided on a medical device that is photoreactive or derivatized to contain a photoreactive moiety. Most organic reactions are carried out between molecules in the ground state. However, photochemical reactions, utilizing light of a specific wavelength range, promote molecules to an electronically excited state. Electrons can move from the ground-state energy level of the molecule to a higher level with this application of outside energy. The physical processes undergone by excited molecules include excitation, vibrational relaxation, intersystem crossing, singlet-singlet transfer or triplet-triplet transfer (photosensitization), and the like.

Some compounds will assume excited triplet states upon excitation by exposure to a certain wavelength of light. These compounds ("sensitizers" or "photosensitizers") can interact with various other compounds ("acceptors") and transfer energy to or electrons from the acceptors, thus returning the sensitizer to its unexcited or ground state. Most compounds will assume the excited singlet upon excitation. A photosensitizer in its triplet state is capable of converting ground-state oxygen (a triplet) to an excited singlet state. See *Singlet Molecular Oxygen*, A. Schaap Ed., Dowden, Hutchinson and Ross, Stroudsburg, Pa. (1976). The singlet oxygen can result in sufficient energy to alter electron states of surrounding materials and to cause bonds in those materials to break.

It is possible to link a photoreactive compound or photosensitizer to a polymer backbone using an appropriate linker, which when exposed to an appropriate light energy, will react to release the therapeutic agent associated therewith. For example, it is possible to bind photosensitizers to therapeutic agents having aliphatic amino groups to form photoreactive/therapeutic agent complexes. Polymer backbones or co-polymer precursors may be derivatized to contain co-polymer side chains or "linkers" having active ester functionalities. The aliphatic amino groups of the complexes may be bound to the active ester functionalities of the polymeric precursors by aminolysis reactions. These stable moieties may be formed into co-polymers to be used as coatings for the medical device. Application of appropriate light energy will result in release of the therapeutic agent from the polymer by breaking a bond to the linker. See, for example, N. L. Krinick et al., *J. Biomater. Sci. Polymer Edn.*, 5(4): 303-324 (1994). Advantageously, the polymers comprise cross-linked matrixes of polymer and include one or more therapeutic agents bound to a surface thereof or incorporated therein. Advantageously, the photochemically reactive group is furfuryl alcohol or meso-chlorin e6 monoethylene diamine disodium salt.

Accordingly, photoreactive agents may be used in conjunction with therapeutic agents linked to a polymeric coating on a medical device. The release of therapeutic agents is controlled by exposure of the coating to an appropriate light energy. Suitable polymers for this embodiment include copolymers of N(-2-hydroxypropyl) methacrylamide and a linker, such as poly(L-lysine-co-polyethylene glycol). Further, non-limiting examples of suitable polymers for this embodiment include poly(propylene glycol) (PPG), poly(vinyl alcohol) (PVA) and poly(acrylic acid) (PAA).

Photosensitizers useful for attachment to a therapeutic agent or linkers include: dabcyl succinimidyl ester, dabcyl sulfonyl chloride, malachite green isothiocyanate, QSY7 succinimidyl ester, SY9 succinimidyl ester, SY21 carboxylic acid succinimidyl ester, SY35 acetic acid succinimidyl ester or the like, which are commercially available from Invitrogen Life Sciences, Carlsbad, Calif. These photoreactive agents will absorb light in the range of from about 450 nm to about 650 nm.

Accordingly, in one embodiment of the invention, a polymeric material and therapeutic agent may be joined by a linking moiety. The linking moiety attaches at a first end to the polymeric material and at a second end via a photochemically reactive group to the therapeutic agent. See, for example, U.S. Pat. Nos. 5,263,992 and 6,179,817, which are herein incorporated by reference. Exposure to light energy will cause the photochemically reactive group to release the therapeutic agent.

In one embodiment, a polymeric material linked via a photoreactive group to a therapeutic agent is exposed to light energy under conditions and for a time to cause the therapeutic agent to be release from the linker at a desired rate. Rate of release can be regulated by increasing the duration and/or intensity of applied light energy. Selection of the appropriate wavelength of light to cause the release will be apparent to one having skill in the art. Preferably, the applied light will not compromise the efficiency of the therapeutic agent or the integrity of the medical device exposed thereto.

In another aspect of the invention, it is possible to bind therapeutic agents having, or derivatized to contain, reactive aliphatic amino groups to polymers having, or derivatized to contain, ester or acid functional groups. The ester or acid moieties may, for example, be present on a polymer or co-polymer side chain. Amidization reaction will bind the aliphatic amino groups of the therapeutic agent to the ester groups on the polymer. Other methods of reversibly adding therapeutic agents or the like to polymers will be known to those having ordinary skill in the art. For example, therapeutic agents having, or derivatized to contain reactive hydroxyl groups, may be attached to polymers having or derivatized to contain ester or acid functional groups.

In a further embodiment of the invention, a linker will include a photoreactive group arranged between a polymeric material and a therapeutic agent. The photoreactive group and therapeutic agent may be embedded in the polymeric material or coated on a surface thereof. The photoreactive group will release the therapeutic agent upon exposure to light in the wavelength range of from about 200 nm to about 800 nm.

Figure 3A:
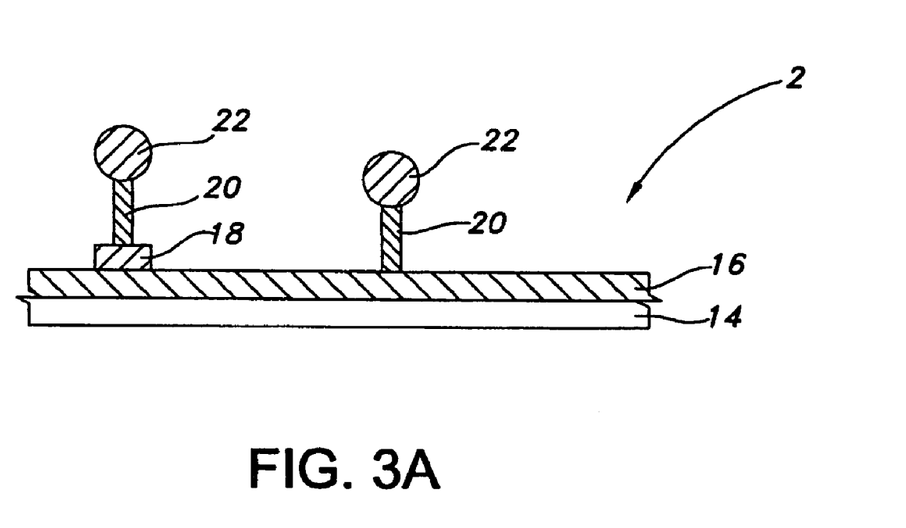
FIGS. 3A and 3B are schematic representations of a cross-section of an embodiment of a coated medical device according to the invention.
Figure 3B:
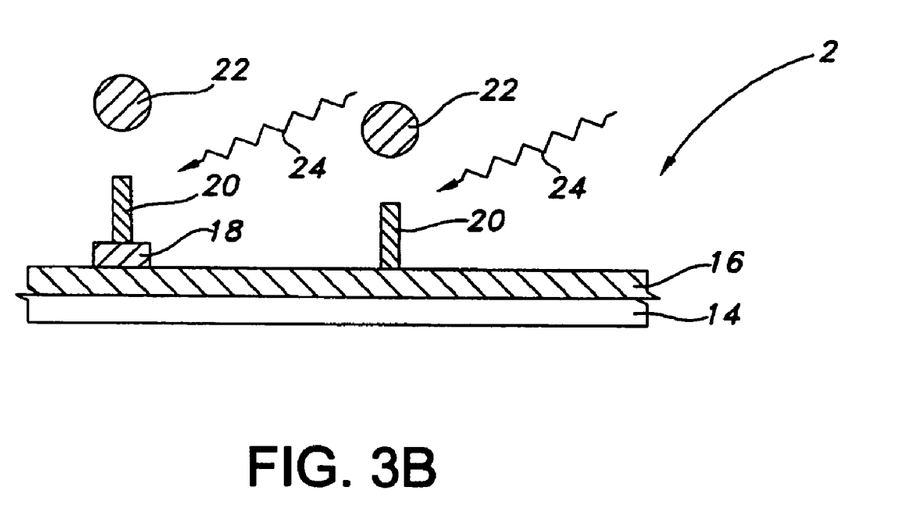

Referring now to FIGS. 3A and 3B, a diagrammatic representation of an embodiment using polymeric materials linked to photoreactive moieties is shown. A surface of a medical device 14 serves as a substrate for a layer of polymeric material 16. A photoreactive linker 20 attaches to the polymeric material 16 either directly or via a reactive group 18. In this embodiment, the free end of the linker includes a photoreactive moiety 20 which is bound to a therapeutic agent 22. As shown in FIG. 3B, upon exposure to an applied energy source 24, the therapeutic agent 22 is released from the polymeric material 16.

Figure 3C:
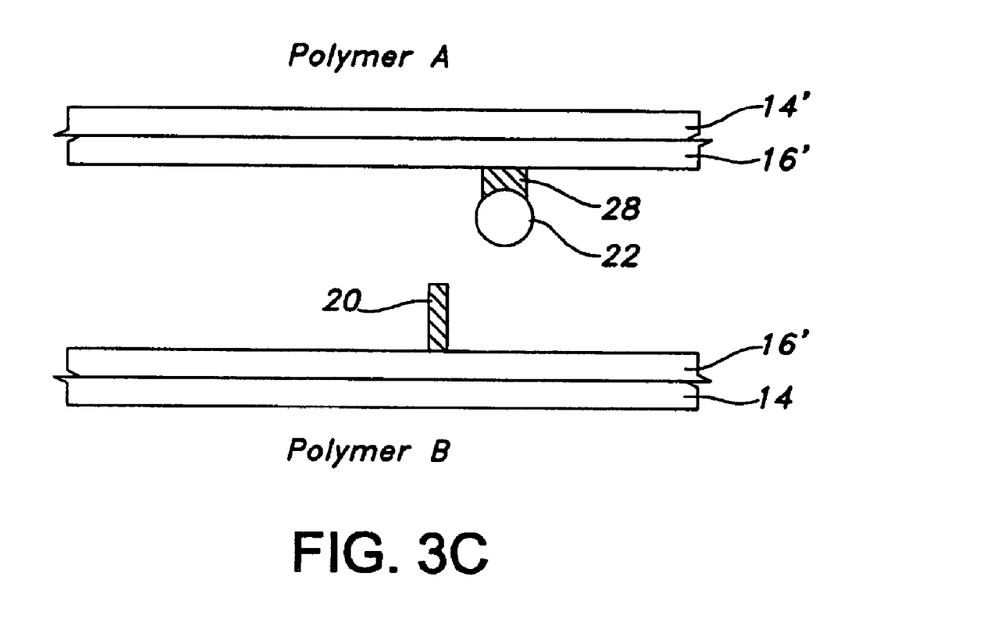
FIGS. 3C and 3D are schematic representations of a cross-section of a further embodiment of a coated medical device according to the invention.
Figure 3D:
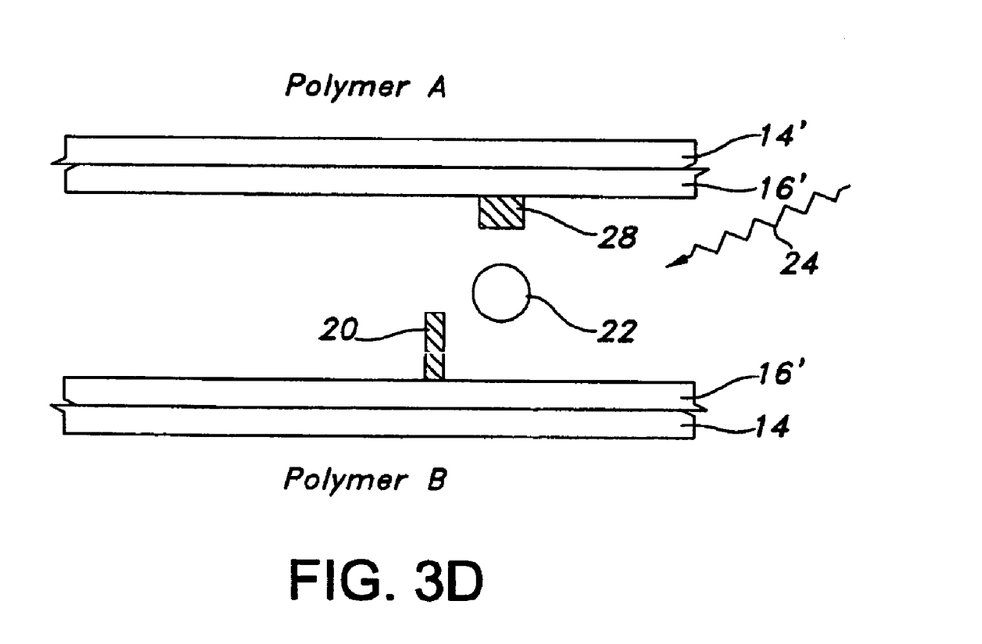

Referring now to FIGS. 3C to 3D, a schematic representation of an alternative embodiment of the invention is shown. In this embodiment, a surface of a medical device 14 serves as a substrate for a layer of polymeric material 16'. The layer 16' includes two miscible polymeric materials labeled polymer A and polymer B. In this embodiment, polymer A includes a photoreactive moiety 20. Polymer B includes a therapeutic agent 22 bound to a linker 28 in the vicinity of photoreactive moiety 20. Upon exposure to an applied energy source 24, the photoreactive moiety 20 reacts with the linker 28 to release the therapeutic agent 22 from Polymer B.

In a still further aspect of the present invention, light reactive drug is contained in polymeric micelles. The micelles may be added as a layer between a medical device substrate and a polymeric matrix or may be integrated into a polymeric coating on the substrate or may be added as a layer on a polymeric coating on the substrate.

Figure 4A:
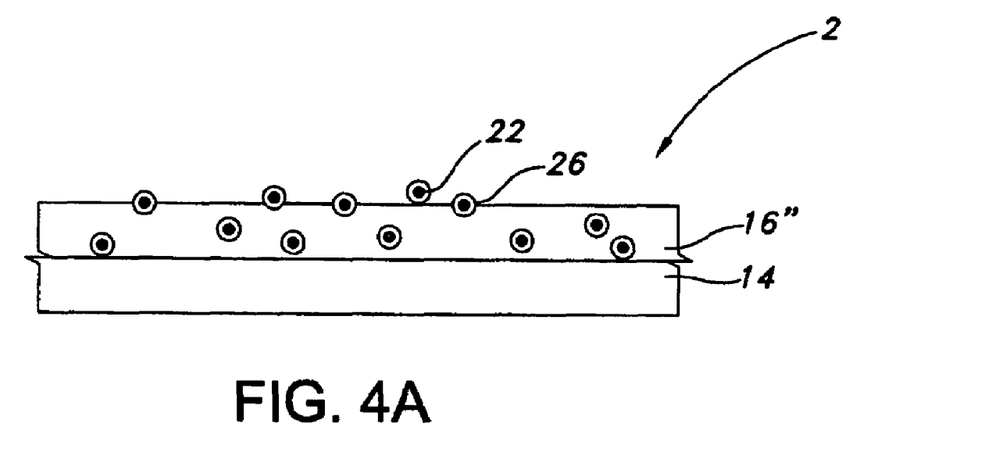
FIGS. 4A and 4B are schematic representations of a cross-section of a further embodiment of a coated medical device according to the invention.
Figure 4B:
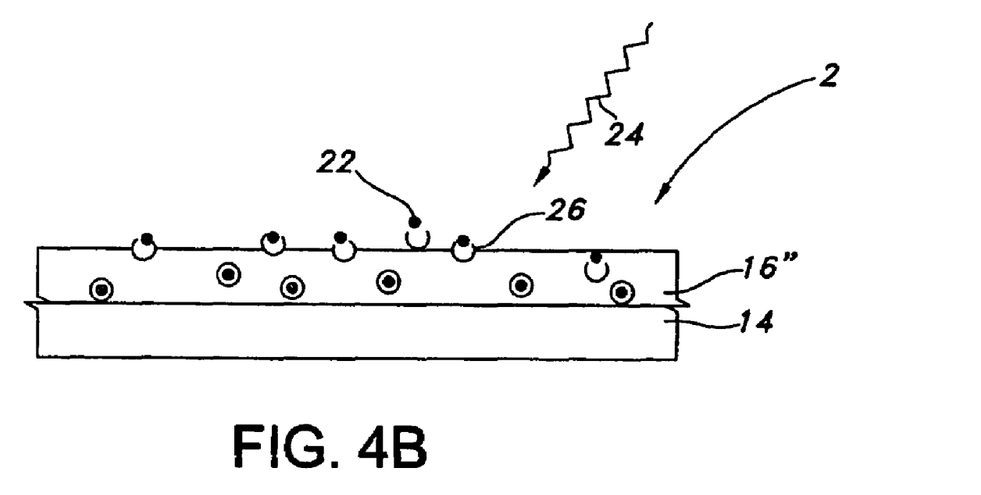

Referring now to FIGS. 4A and 4B, a schematic representation of yet a further embodiment is shown. In this embodiment, a surface of a medical device 14 is coated with a polymeric material 16". The material 16" is embedded and/or coated with micelles 22 having therapeutic agent 26 contained therein. Upon exposure to an appropriate applied energy source 24 the micelle 22 expands or opens so as to release the therapeutic agent 26 held therein. Preferably, the therapeutic agent is also photoreactive or derivatized to be photoreactive.

Suitable Therapeutic Agents

Both water-soluble and water-insoluble therapeutic agents will find use in the coatings covered by the invention. For purposes for this application, the terms water-soluble and water-insoluble therapeutic agent will have the following definitions. Water-soluble therapeutic agent will mean that up to 30 parts of solvent are required to completely dissolve one part of therapeutic agent. The term water-insoluble therapeutic agent will mean greater than 30 parts of solvent are required to dissolve one part of the therapeutic agent. For further discussion of these terms, see U.S. Pharmacopia, National Formulary, latest edition, incorporated herein by reference.

Examples of suitable therapeutic agents include, without limitation, thrombo-resistant agents, anti-microbial agents, anti-tumor agents, anti-viral agents, cell cycle regulating agents, their homologs, derivatives, fragments, pharmaceutical salts, and combinations thereof. Preferably, the therapeutic agent is an antimicrobial agent. More preferably, the therapeutic agent is photoreactive or derivatized to contain a photoreactive moiety.

Useful anti-thrombogenic agents may include, for example, heparin, heparin sulfate, hirudin, chondroitin sulfate, dermatan sulfate, keratin sulfate, lytic agents, including urokinase and streptokinase, their homologs, analogs, fragments, derivatives and pharmaceutical salts thereof.

Useful antimicrobial agents may include, for example, penicillins, cephalosporins, vancomycins, aminoglycosides, quinolones, polymyxins, erythromycins, tetracyclines, chloramphenicols, clindamycins, lincomycins, sulfonamides, their homologs, analogs, fragments, derivatives, pharmaceutical salts and mixtures thereof.

Useful anti-tumor agents may include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide; their homologs, analogs, fragments, derivatives, pharmaceutical salts and mixtures thereof Useful anti-viral agents may include, for example, amantadines, rimantadines, ribavirins, idoxuridines, vidarabines, trifluridines, acyclovirs, ganciclovirs, zidovudines, foscarnets, interferons, their homologs, analogs, fragments, derivatives, pharmaceutical salts and mixtures thereof.

While the foregoing therapeutic agents have been used to prevent or treat various conditions, they are provided by way of example and are not meant to be limiting, as other therapeutic agents may be developed which are equally applicable for use with the present invention.

The rate of release of the therapeutic agent will be controlled by the intensity, frequency and duration of ultrasound energy or light energy to which the polymeric structure containing the therapeutic agent is exposed. The rate of release will also be controlled by the area of the medical device exposed to the energy. A principle limitation upon the therapeutic agent is that it neither be degraded nor rendered substantially inactive while being loaded into the polymeric coating or being exposed to the applied ultrasound or light energy source. Furthermore, the therapeutic agent should not react with the polymeric material in which it is contained. Generally, the amount of therapeutic agent present in a coating of the invention will be greater than the standard single dose for the therapeutic agent to be administered preferably orders of magnitude greater than the standard single dose. Proportions of the therapeutic agent that are suitable for the purposes of the invention range generally from about 0.1 to about 70 parts by weight of the coating, with the balance being the polymeric component.

Methods of Making and Using Coatings

The coating is prepared according to the invention by dissolving the polymeric material in a solvent to form a first and combining this first solution with a solution or suspension containing a the therapeutic agent. Preferably, these may be combined at room temperature or at a slightly elevated temperature with the aid of agitation. It is preferred to employ solvents which readily evaporate from the coating at room temperature, or at an elevated temperature below that which inactivates the therapeutic agent.

Where the therapeutic agent used is insoluble in the dissolved polymer material, it is preferred that the agent be very finely subdivided, as by grinding with a mortar and pestle. A preferred form is micronized, e.g., a powder wherein all particles are of a size of 5 mircons or less.

The coating may be preferred by first dissolving the polymeric material such as a biomedical polyurethane in a solvent. The therapeutic agent is then dissolved in the same or a different solvent. Solvents used in making the coating will depend upon the specific polymeric material and therapeutic agent or combination of agents. For example, useful solvents include acetic acid, methyl acetate, ethyl acetate, hexane, N—N dimethylacetamide (DMAC), tehahydrofuram (THF), alcohols, water, N-methylpyrrolidone (NMP) or N-ethyl pyrrolidone (NEP) and combinations thereof.

Certain desired solvents for the polymeric material may not be good solvents for a therapeutic agent of choice. In this case, a solvent is selected which will dissolve the therapeutic agent and be miscible with the solvent for the polymeric material. Thus, a solvent solution of the therapeutic agent may be combined with a polymeric material in solution, and the two solutions may then be combined to form a uniform mixture.

A polymeric matrix may be formed by admixing powdered polymer and therapeutic agents together and melting the mixture to a liquid form which can then be applied by dip coating to the medical device.

Alternatively, a polymeric matrix may be admixed with an appropriate solvent to form a solution. The therapeutic agent may then be added to the solution which can then be applied to the medical device using conventional methods such as dip coating or spray coating. The solvent may be driven off in a drying process, leaving behind the polymeric coating.

In one aspect of the invention, the polymers are block polymers formed into circular micelles. See, for example, Kim et al., *J. of Controlled Release*, 65(3), 345-358 (2000). The micelles so formed are large enough to accommodate therapeutic agents. Once formed, the micelles are loaded with the agent using a known dialysis method. See, for example, Kwon, et al., *J. Controlled Release*, 29, 17-23 (1994). Afterwards, the solution may be treated so as to remove unloaded drug and aggregated particles, for example using centrifugation. The micelles so formed may be freeze dried for storage or mixed with a solvent or formed into a hydrogel or polyamine matrix for application onto the TIVAD, either alone or associated further with a polymeric matrix as described previously.

Accordingly, in an alternate embodiment, circular micelles surrounding a therapeutic agent are added to a polymeric material and the mixture applied as a coating onto the medical device. A diagrammatic representation of this embodiment is shown in FIGS. 4A and 4B. The medical device 14 includes a polymeric material 16 including mycelles 26 containing therapeutic agent 22. The mycelles 26 are shown evenly distributed in the polymeric material 16, where they may be trapped in pore structures, captured in enlarged polymeric chains, or residing at the surface of the polymeric material 16. Upon application of an energy source 24 as shown in FIG. 4B, the myselles release the therapeutic agent therefrom.

An implantable medical device may be coated with the polymeric coating of the invention and implanted into a patient in need thereof. Suitable coating methods will depend upon the particular polymeric material used, and will be apparent to one having ordinary skill in the art. Conventional coating methods such as dip coating, spray coating or dip casting may be used.

Use of the Medical Devices of the Invention

Once implanted, the medical device is subjected to an energy source to increase the therapeutic agent kinetics and/or degrade the polymer so as to release the therapeutic agent contained therein. The energy required to control the rate and duration of release of the therapeutic agent can readily be adjusted.

The optimal energy for producing a safe and effective dosage will depend on the particular polymeric structure and therapeutic agent used. In order to assure safe levels of release of the therapeutic agent, it is possible to test the implant in a liquid medium designed to mimic the in vivo environment and observe the rate of release of the therapeutic agent upon exposure to known levels of energy. In this way, a curve of applied energy versus therapeutic agent release rate can be derived. The coating can be made to deliver a predetermined rate of release of the therapeutic agent by selection of an appropriate intensity and duration of applied energy, based on the curve.

It is possible to use different photoreactive polymers with different therapeutic agents, so that exposure to a first light energy source will release a first therapeutic agent while exposure to a second (i.e., different frequency) light energy source will only release a second therapeutic agent. Similarly, it is possible to use different polymer coatings having different therapeutic agents contained therein, so that exposure to a light energy source will only release a first therapeutic agent while exposure to an ultrasound energy source will release a second therapeutic agent.

For exposure of the medical device to ultrasonic energy, a commercially available ultrasonic transducer may be used by placement of the ultrasound device on a surface of the skin over the implanted device. Desirably, a coupling media is placed between the ultrasound device and the skin to improve conveyance of the ultrasound energy. Suitable coupling agents are known to those in the art.

For exposure of the implanted medical device to light energy, a light source emitting the appropriate wavelength of light including a probe for intradermal insertion may be used. Such probes are disclosed, for example, in U.S. Pat. No. 6,620,154 to Amirkhanian et al. The probe may be used to administer laser treatment to a surface of an implanted medical device by insertion intradermally either directly above the medical device or inside the medical device.

EXAMPLE 1

Ultrasound Activatable Micelles

This example describes a coating made with a cross-linked polymeric material formed into micelles loaded with therapeutic agent that will release the agent upon exposure to ultrasound energy. An amphiphylic alternating copolymer consisting of poly(ethyleneglycol) and poly(L-lactic acid) as shown below is used to form micelles. The polymeric micelles are further stabilized by polymerization using N,N-diethylacrylamide in a poly(L-lactic acid) inner core of the micelles. The micelles are further optimized by reaction of acetylated hydroxyalkyl carboxylic acid derivatives to add functional groups, such as —COOH, $SO_4$, H, NH or the like, as attachment sites for the therapeutic agent.

PLA-PEG-PLA triblock copolymer

The hydrophilic/hydrophobic copolymer is dissolved in methylene chloride and emulsified with a 5% aqueous solution of albumin containing an antibiotic and/or a thrombogenic agent by sonicating for 2 minutes, and spray-drying to produce particles (10 μm). The micelle hydrogel microparticles are redissolved in an aqueous solution of sodium chloride. The polymeric micelle composition is dip coated and/or spray coated onto an inner surface, outer surface or both of the TIVAP to form the coated medical device. Release of the therapeutic agent is accomplished by the application of ultrasound energy on the surface of the skin over the implant. The ultrasound energy is in the frequency range of from about 20 KHz to about 90 KHz for from about 0.1 seconds to about 20 seconds. The therapeutic agent is released from the core of the micelles and available to the surrounding tissue.

EXAMPLE 2

Ultrasound Activatable Micelles

This example describes a coating made with a cross-linked polymeric material which forms micelles loaded with therapeutic agent that will release the agent upon exposure to ultrasound energy. Poly(ethylene oxide glycol)/poly(propylene oxide glycol) copolymers and poly(E-capriolactone) are used to form a block polymer as shown below.

PEG/PEP/PEG/PCL

The core of this polymeric micelle is stabilized by forming an interpenetrating cross-linked system using N,N,diethylacrylamide as a cross-linking agent. The therapeutic agent is incorporated into the micelle as described above. The micelle is dried and used directly as a coating on a medical device substrate or is dried and applied onto a polymeric coating on the substrate.

EXAMPLE 3

Ultrasound Activatable Micelles

This example describes a coating made with a cross-linked polymeric material which forms micelles loaded with therapeutic agent that will release the agent upon exposure to ultrasound energy. A commercially available poly(ethylene/glycol)-poly(propylene glycol) triblock copolymer (PEO-PPO-PEO), as shown below is used to make the polymeric material of the coating. The copolymer is optionally cross-linked to form an interpenetrating network.

To a commercial polymer, (PLURONIC 105 or PLURONIC 127, available from BASF Corp., Ludwigshafen, Germany) is added N,N-diethylacrylamide to stabilize the hydrophobic core of the micelle. The therapeutic agent is incorporated into the micelle as described above. The micelles are dried and used directly as a coating on a medical device substrate or are dried and appied onto a polymeric coating on the substrate.

EXAMPLE 4

Light Activatable Coating

This example describes a coating made with a polymeric material including therapeutic agent which is attached by light reactive pendant chains to a surface of a medical device, wherein the coating will release the agent upon exposure to light energy. A water soluble copolymer of N-(2-hydroxypropyl) methacrylamide and a photoreactive oligopeptide containing a therapeutic agent are provided as shown below.

A solution of the water-soluble copolymer is applied to at lease one of the inside and outside surfaces of the TIVAD. Release of the therapeutic agent is accomplished by the application of 650 nm wavelength light to the TIVAD for 60 seconds, to the surface of the skin surface over the implant. The light penetrates the skin to activate release of the drug from the oligopeptide. Alternatively, a light probe is inserted into the port via the septum to introduce light directly into the reservoir of the port. The release rate is a function of the light exposure time.

It will be apparent that the present invention has been described herein with reference to certain preferred or exemplary embodiments. The preferred or exemplary embodiments described herein may be modified, changed, added to, or deviated from without departing from the intent, spirit and scope of the present invention, and it is intended that all such additions, modifications, amendments and/or deviations be included within the scope of the following claims.

All publications, patents, and patent applications referenced in this specification are incorporated herein by reference to the same extent as if each individual publication, patent, or application had been specifically and individually indicated to be incorporated herein by reference.

What is claimed is:

1. An implantable medical device comprising:
   a vascular access device; and
   a light reactive coating on at least one of an inner surface and an outer surface of said vascular access device, said coating comprising: (a) a polymeric component (b) a photoreactive linker including a photosensitizer; and (c) at least one therapeutic agent releasably associated with said photoreactive linker,
   wherein said photoreactive linker is attached at a first end to said polymeric component and at a second end to said therapeutic agent and wherein a rate of release of said therapeutic agent from said photoreactive linker is controlled by in situ exposure of the medical device to a light source; and wherein said vascular access device is a total implantation venous access device (TI VAD).

2. The device of claim 1, wherein said coating is an ultrasound reactive coating.

3. The device of claim 2, wherein said ultrasound reactive coating releases said therapeutic agent upon exposure to continuous or pulsed ultrasonic energy in the frequency range of from about 20 KHz to about 500 KHz.

4. The device of claim 3, wherein a rate of release of said coating is controlled by at least one of: a duration of exposure to said ultrasonic energy, a frequency of said ultrasonic energy and an intensity of said ultrasonic energy.

5. The device of claim 3, wherein said polymeric component comprises a polymer selected from the group consisting of:
   (a) a poly(ethylene oxide) (PEO), poly(ethylene glycol) (PEG), poly(propylene glycol) (PPG), poly (L-lactic acid) (PLLA), poly(caprolactone), poly(α-amino acids), polyurethanes, poly(vinyl alcohol) (PVA) poly (vinyl pyrrolidone), poly hydroethyl methacrylate, and copolymers and block polymers thereof or
   (b) poly(L-lysine-co-polyethyleneglycol), poly[(L-lactide-co-methenyl-capped oligo(ethylene oxide) methacrylate and cross-linked dextran-polyethylene glycol hydrogels and co-polymers and block polymers thereof.

6. The device of claim 2, wherein said therapeutic agent is at least one of a thrombo-resistant agent, an antimicrobial agent, an anti-tumor agent, an anti-fungal agent and an anti-viral agent.

7. The device of claim 6, wherein said therapeutic agent is at least one of a penicillin, a cephalosporin, a vancomycin, an aminoglycoside, a quinolone, a polymyxin, an erythromycin, a tetracycline, a chloramphenicol, a clindamycin, a lincomycin, a sulfonamide, or a homolog, an analog, a fragment, a derivative or a pharmaceutically acceptable salt thereof.

8. The device of claim 1, wherein said light reactive coating releases said therapeutic agent upon exposure to a light source having a wavelength range of from about 200 nm to about 800 nm.

9. The device of claim 1, wherein a rate of release of said therapeutic agent from said coating is controlled by at least one of: a duration of exposure to said light source, a wavelength of said light source and an intensity of said light source.

10. The device of claim 1, wherein said polymeric component is selected from the group consisting of: poly(ethylene oxide) (PEO), poly(ethylene glycol) (PEG), poly (propylene glycol) (PPG), poly (L-lactic acid) (PLLA), poly(caprolactone), poly($\alpha$-amino acids), polyurethanes, poly(vinyl alcohol) (PVA) poly(vinyl pyrrolidone), poly hydroethyl methacrylate, and copolymers and block polymers thereof.

11. The device of claim 1, wherein said therapeutic agent is at least one of a thrombo-resistant agent, an antimicrobial agent, an anti-tumor agent, an anti-fungal agent and an anti-viral agent.

12. The device of claim 1, wherein said therapeutic agent is at least one of a penicillin, a cephalosporin, a vancomycin, an aminoglycoside, a quinolone, a polymyxin, an erythromycin, a tetracycline, a chloramphenicol, a clindamycin, a lincomycin, a sulfonamide, or a homolog, an analog, a fragment, a derivative or a pharmaceutically acceptable salt thereof.

13. The device of claim 1, wherein said linker is bound to a backbone of said polymeric component and links the photosensitizer to the backbone.

14. The device of claim 1, wherein said photoreactive linker is attached at its second end via the photosensitizer to the therapeutic agent.

15. The device of claim 1, wherein said light reactive coating releases said therapeutic agent upon exposure to a light source having a wavelength range of from about 450 nm to about 650 nm.

16. A method of releasing a therapeutic agent from an implanted medical device, comprising the steps of:
    (a) implanting a medical device according to claim 1 intradermally into a patient in need thereof; and
    (b) releasing said therapeutic agent to said patient by extra-dermal exposure to a light energy source.

17. The method of claim 16, further comprising the step of:
    (c) controlling a rate of release of said therapeutic agent from said coating by application of said light energy source for a predetermined period of time.

18. The method of claim 17, wherein said releasing step is extra- dermal exposure to an ultrasonic energy source.

19. The method of claim 17, wherein said ultrasonic energy source comprises continuous or pulsed ultrasonic energy in the frequency range of from about 20 KHz to about 500 KHz.

20. The method of claim 17, wherein said light energy source comprises light energy in the wavelength range of from about 200 nm to about 800 nm.

21. The method of claim 17, wherein said light energy source comprises light energy in the wavelength range from about 450 nm to about 650 nm.

* * * * *

UNITED STATES PATENT AND TRADEMARK OFFICE
CERTIFICATE OF CORRECTION

| | |
|---|---|
| PATENT NO. | : 7,356,368 B2 |
| APPLICATION NO. | : 10/896193 |
| DATED | : April 8, 2008 |
| INVENTOR(S) | : Sharon Mi Lyn Tan |

Page 1 of 1

It is certified that error appears in the above-identified patent and that said Letters Patent is hereby corrected as shown below:

At column 3, line 10, the printed patent should read: "...needed by the patient.".

At column 12, line 9, the printed patent should read: "...induced by the sound field.".

At column 15, line 58, the printed patent should read: "...agent to be released from..".

At column 18, line 5, the printed patent should read: "...containing the therapeutic agent.".

At column 21, lines 61-62, the printed patent should read: "...applied to at least one of the...".

Signed and Sealed this

Fifteenth Day of July, 2008

JON W. DUDAS
*Director of the United States Patent and Trademark Office*